(12) United States Patent  (10) Patent No.: US 8,114,148 B2
Atanasoska et al.  (45) Date of Patent: Feb. 14, 2012

(54) MEDICAL DEVICES FOR DELIVERY OF THERAPEUTIC AGENT IN CONJUNCTION WITH GALVANIC CORROSION

(75) Inventors: Liliana Atanasoska, Edina, MN (US); Jan Weber, Maastricht (NL); Paul Grosso, Maple Grove, MN (US); Robert W. Warner, Woodbury, MN (US); Kasyap V. Seethamraju, Eden Prairie, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 252 days.

(21) Appl. No.: 12/489,948

(22) Filed: Jun. 23, 2009

(65) Prior Publication Data

US 2009/0326638 A1 Dec. 31, 2009

Related U.S. Application Data

(60) Provisional application No. 61/075,446, filed on Jun. 25, 2008.

(51) Int. Cl.
*A61F 2/82* (2006.01)
(52) U.S. Cl. .................................... 623/1.15; 623/1.43
(58) Field of Classification Search ........ 623/1.11–1.15, 623/1.42–1.48; 252/512
See application file for complete search history.

(56) References Cited

U.S. PATENT DOCUMENTS

| 5,360,440 A | 11/1994 | Andersen |
| 5,614,549 A | 3/1997 | Greenwald et al. |
| 5,733,925 A | 3/1998 | Kunz et al. |
| 6,287,484 B1 * | 9/2001 | Hausslein et al. ............ 252/512 |
| 6,599,580 B2 | 7/2003 | Muffoletto et al. |
| 6,730,699 B2 | 5/2004 | Li et al. |
| 6,884,817 B2 | 4/2005 | Li et al. |

(Continued)

FOREIGN PATENT DOCUMENTS

WO 2006108065 A2 10/2006

(Continued)

OTHER PUBLICATIONS

N. R. James et al., "Polyurethanes with radiopaque properties", Biomaterials 27 (2006) 160-166.

(Continued)

*Primary Examiner* — Suzette J Gherbi
(74) *Attorney, Agent, or Firm* — Mayer & Williams PC; David B. Bonham; Keum J. Park

(57) ABSTRACT

According to an aspect of the present invention, at least one ionic therapeutic agent is delivered from an implantable or insertable medical device that comprises an ion-conductive polymeric region that is disposed on a metallic region. The metallic region is in electrical contact with a dissimilar metallic region, such that a galvanic current is generated by the dissimilar metals when the device is implanted or inserted into a patient. Delivery of the ionic therapeutic agent from the ion-conductive polymeric region may be, for example, either accelerated or retarded by the galvanic current. According to another aspect of the present invention, implantable or insertable medical devices are provided which comprise: (a) a first metallic region having a first corrosion potential, (b) a second metallic region in electrical contact with the first metallic region and having a second corrosion potential that is greater than the first corrosion potential, and (c) a solid ion-conductive polymeric region, comprising an ion conducting polymer and an ionic therapeutic agent, disposed on the first metallic region, the second metallic region, or both.

25 Claims, 2 Drawing Sheets

U.S. PATENT DOCUMENTS

| | | | |
|---|---|---|---|
| 7,582,112 B2* | 9/2009 | Scheuermann et al. | 623/1.46 |
| 2002/0004060 A1 | 1/2002 | Heublein et al. | |
| 2002/0082679 A1* | 6/2002 | Sirhan et al. | 623/1.15 |
| 2003/0060873 A1 | 3/2003 | Gertner et al. | |
| 2003/0236514 A1 | 12/2003 | Schwarz | |
| 2004/0034409 A1 | 2/2004 | Heublein et al. | |
| 2005/0209680 A1 | 9/2005 | Gale et al. | |
| 2005/0261760 A1 | 11/2005 | Weber | |
| 2006/0184092 A1 | 8/2006 | Atanasoska et al. | |
| 2006/0198869 A1 | 9/2006 | Furst et al. | |
| 2006/0271168 A1 | 11/2006 | Kleine et al. | |
| 2008/0161906 A1 | 7/2008 | Atanasoska et al. | |
| 2008/0262412 A1* | 10/2008 | Atanasoska et al. | 604/20 |
| 2009/0088834 A1* | 4/2009 | Wang | 623/1.15 |
| 2010/0008970 A1* | 1/2010 | O'Brien et al. | 424/426 |
| 2010/0272595 A1* | 10/2010 | Maziasz et al. | 420/45 |
| 2010/0331760 A1* | 12/2010 | Atanasoska et al. | 604/20 |
| 2011/0046539 A1* | 2/2011 | Atanasoska et al. | 604/20 |

FOREIGN PATENT DOCUMENTS

| | | |
|---|---|---|
| WO | 2008036549 A2 | 3/2008 |

OTHER PUBLICATIONS

S.C. Dexter, "Galvanic Corrosion," Mas Note, 2003, 2 pp.

B. Nottelet et al, "Synthesis of an X-ray opaque biodegradable copolyester by chemical modification of poly (e-caprolactone)", Biomaterials 27 (2006) 4948-4954.

M. Bitar et al., "Soluble phosphate glass fibres for repair of bone-ligament interface", Journal of Materials Science: Materials in Medicine 16 (2005) 1131-1136.

H.N.T. Le et al, "Corrosion protection and conducting polymers: polypyrrole films on iron", Electrochimica Acta 46 (2001) 4259-4272.

L. Cecchetto et al., "On the mechanism of the anodic protection of aluminium alloy AA5182 by emeraldine base coatings Evidences of a galvanic coupling", Electrochimica Acta 52 (2007) 3485-3492.

M. Rohwerder et al, "Conducting polymers for corrosion protection: What makes the difference between failure and success'?", Electrochimica Acta 53 (2007) 1300-1313.

S.U. Rahman et al., "Thermal effects on the process of electropolymerization of pyrrole on mild steel", Synthetic Metals 140 (2004) 207-223.

M. Sokolsky-Papkov et al., "Polymer carriers for drug delivery in tissue engineering", Advanced Drug Delivery Reviews 59 (2007) 187-206.

Galvanic Series, downloaded from http://corrosionsource.com/handbook/galv_series.htm on May 15, 2007, 2 pp.

Liang W-J. et al., "Morphology and Ionic Conductivity Studies of Hybrid Electrolytes based on Epoxide-Crosslinked Polysilane/Polyether Networks," Macromol. Chem. Phys. 2004, 205, 600-610.

C.P. Fonseca et al., "Development of a biodegradable polymer electrolyte for rechargeable batteries," Journal of Power Sources 155 (2006) 381-384.

C.P. Fonseca et al., "Thermal and Conduction Properties of a PCL-biodegradable Gel Polymer Electrolyte with $LiClO_4$, $LiF_3CSO_3$, and $LiBF_4$ Salts," Int. J. Electrochem. Sci., 2 (2007) 52-63.

K, Shinyama et al., Proceedings of the 7th International Conference on Properties and Applications of Dielectric Materials, Jun. 1-5, 2003 Nagoya, Japan, 707-710.

V. Maquet et al., "Characterization of Porous Polylactide Foams by Image Analysis and Impedance Spectroscopy," Langmuir 2000, 16, 10463-10470.

P. Gomez-Romero et al., "Hybrid Organic-Inorganic Materials—In Search of Synergic Activity," Adv. Mater. 2001, 13, No. 3, Feb. 5, 163-174.

Zhonghua Peng, "Rational Synthesis of Covalently Bonded Organic-Inorganic Hybrids," Angew. Chem. Ind. Ed., 2004, 43, 930-935.

F.A. Beleze et al., "Synthesis and Characterization of Organic-Inorganic Hybrids Formed between Conducting Polymers and Crystalline Antimonic Acid," J. Braz. Chem., vol. 12, No. 4, 542-547, 2001.

M.J. MacLachlan et al., "New (Inter)Faces: Polymers and Inorganic Materials," Adv. Mater., 2000, 12, No. 9, 675.

R. Duncan et al., "Polymer—drug conjugates, PDEPT and PELT: basic principles for design and transfer from the laboratory to clinic," Journal of Controlled Release 74 (2001) 135-146.

Duncan, "The Dawning Era of Polymer Therapeutics", Nature Reviews/Drug Discovery, vol. 2, May 2003, 347.

J. G. Qasem et al, AAPS PharmSciTech 2003, 4(2) Article 21.

E.W. Damen et al., "Paclitaxel esters of malic acid as prodrugs with improved water solubility," Bioorg. Med. Chem., Feb. 2000, 8(2), pp. 427-432.

C. Li, "Poly(L-glutamic acid)—anticancer drug conjugates," Advanced Drug Delivery Reviews 54 (2002) 695-713.

J. Fan et al., "Composite polymer electrolytes using surface-modified fumed silicas: conductivity and rheology", Solid State Ionics 111 (1998) 117-123.

* cited by examiner

MEDICAL DEVICES FOR DELIVERY OF THERAPEUTIC AGENT IN CONJUNCTION WITH GALVANIC CORROSION

RELATED APPLICATIONS

This application claims priority from U.S. provisional application 61/075,446, filed Jun. 25, 2008, which is incorporated by reference herein in its entirety.

FIELD OF THE INVENTION

The present invention relates to medical devices, and more particularly to medical devices that deliver therapeutic agents.

BACKGROUND OF THE INVENTION

Medical devices are known which utilize electrical potential to enhance drug delivery.

For example, medical devices are known which deliver drugs by iontophoresis, a process by which an electric field is used as a driving force to transport a drug into a subject. This technique typically requires two or more electrodes for creating an electric field as well as a drug that carries a net electrical charge at the local physiological pH.

As another example, medical devices are also known which rely on electroporation to enhance drug delivery to cells. The electroporation method uses short, high-voltage pulses to create transient pores in the cell membranes or in organelles within the cells. This transient, permeabilized state can be used to load cells and organelles with a wide variety of therapeutic agents, for example, genes, proteins, small molecule drugs, dyes, tracers, and so forth.

SUMMARY OF THE INVENTION

According to an aspect of the present invention, at least one ionic therapeutic agent is delivered from an implantable or insertable medical device that comprises an ion-conductive polymeric region that is disposed on a metallic region. The metallic region is in electrical contact with a dissimilar metallic region, such that a galvanic current is generated by the dissimilar metals when the device is implanted or inserted into a patient. Delivery of the ionic therapeutic agent from the ion-conductive polymeric region may be, for example, either accelerated or retarded by the galvanic current.

According to another aspect of the present invention, implantable or insertable medical devices are provided which comprise: (a) a first metallic region having a first corrosion potential, (b) a second metallic region in electrical contact with the first metallic region and having a second corrosion potential that is greater than the first corrosion potential, and (c) a solid ion-conductive polymeric region, comprising an ion conducting polymer and an ionic therapeutic agent, disposed on the first metallic region, the second metallic region, or both.

An advantage of the present invention is that implantable and insertable medical devices may be provided in which therapeutic agent delivery is electrically assisted, without the need for an external source of electric power.

These and other aspects, embodiments and advantages of the present invention will become readily apparent to those of ordinary skill in the art upon review of the Detailed Description and Claims to follow.

DETAILED DESCRIPTION

Figure 1:
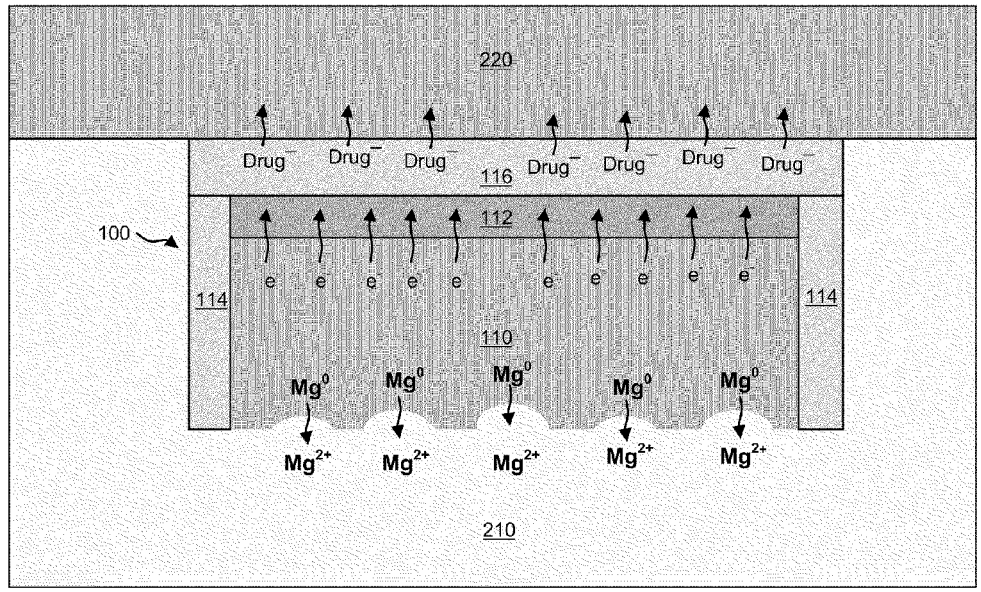
FIG. 1 is a schematic cross-sectional illustration of a medical device in accordance with an embodiment of the present invention, disposed in a blood vessel.

According to an aspect of the present invention, at least one ionic therapeutic agent is delivered from an implantable or insertable medical device that comprises an ion-conductive polymeric region disposed on a metallic region. The metallic region is in electrical contact with a dissimilar metallic region, such that a galvanic current is generated by the dissimilar metals when the device is implanted or inserted into a patient. Delivery of the ionic therapeutic agent from the ion-conductive polymeric region may be, for example, either accelerated or retarded by the galvanic current.

According to another aspect of the present invention, implantable or insertable medical devices are provided which comprise: (a) a first metallic region having a first corrosion potential, (b) a second metallic region in electrical contact with the first metallic region and having a second corrosion potential that is greater than the first corrosion potential, and (c) a solid ion-conductive polymeric region, comprising an ion conducting polymer and an ionic therapeutic agent, disposed on the first metallic region, the second metallic region, or both.

"Therapeutic agents," "drugs," "bioactive agents," "pharmaceuticals," "pharmaceutically active agents," and other related terms may be used interchangeably herein and include genetic and non-genetic therapeutic agents. Therapeutic agents may be used singly or in combination.

Examples of implantable or insertable medical devices may be selected, for example, from the following, among others: stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglielmi detachable coils and metal coils), septal defect closure devices, drug depots that are adapted for placement in an artery for treatment of the portion of the artery distal to the device, myocardial plugs, patches, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, or other devices that are implanted or inserted into the body for treatment or diagnostic purposes.

A further example of a device in is a drug delivery device, such as a pill or suppository, which may be taken orally or inserted into another body orifice. These devices, as well as the many other devices described herein, may be made along the lines described herein (e.g., as described in conjunction with FIGS. 1-4 below, among other techniques). Moreover, a sugar coating and/or a lubricious coating may be provided around the device to delay the corrosion until the device is positioned at its destination.

Medical devices in accordance with the present invention are adapted for delivery of therapeutic agents, particularly ionic therapeutic agents. The implantable and insertable medical devices of the invention can be used for diagnosis and treatment, including systemic diagnosis and treatment and localized diagnosis and treatment of various tissues and organs. Non-limiting examples are tumors; organs including the heart and coronary and peripheral vascular system (referred to overall as "the vasculature") including various arteries (e.g., coronary, femoral, aorta, iliac, carotid and vertebrobasilar arteries) and veins, the urogenital system, including kidneys, bladder, urethra (including prostatic urethra), ureters, prostate, vagina, uterus and ovaries, spermatic and fallopian tubes, the nasolacrimal duct, biliary duct, the eustachian tube, lumens of the lymphatic system, the major body cavities (peritoneal, pleural, pericardial), eyes, ears, spine, nervous system, trachea, bronchi, nasal passages and sinuses, esophagus, stomach, duodenum, small intestine, large intestine, colon, rectum, brain, liver, pancreas (including the pancreatic duct system), skeletal muscle, smooth muscle, breast, dermal tissue, cartilage, tooth and bone, among others.

As used herein, "treatment" refers to the prevention of a disease or condition, the reduction or elimination of symptoms associated with a disease or condition, or the substantial or complete elimination of a disease or condition.

Preferred subjects are vertebrate subjects, for example, humans, livestock and pets.

As noted above, in the medical devices of the present invention, delivery of an ionic therapeutic agent may be, for example, either accelerated or slowed by galvanic current that is generated by dissimilar metallic regions. Galvanic current flows when two or more dissimilar metallic materials are brought into electrical contact in an aqueous environment. Potentials of various metallic materials can be measured in aqueous environments (e.g., fresh water, sea water, blood, urine, other biological fluids, etc.) vs. a suitable reference electrode (e.g., a Saturated Calomel Electrode, standard hydrogen electrode (SHE), Cu/CuSO$_4$ reference electrode, etc.) and tabulated. Such potentials are sometimes called corrosion potentials. A collection of such measurements for differing materials is sometimes referred to as a galvanic series. For example, the following are some published values for various metallic materials (e.g., metals and metal alloys) in flowing seawater vs. a Saturated Calomel Electrode (SCE):

magnesium (−1.60 to −1.63V)
zinc (−0.98 to −1.03V)
aluminum alloys (−0.70 to −0.90V)
cast irons (−0.60 to −0.72V)
steel (−0.60 to −0.70V)
copper (−0.28 to −0.36V)
silver (−0.09 to −0.14V)
300 Series stainless steels (−0.00 to −0.15V)
titanium and its alloys (0.06 to −0.05V)
Inconel 625 (+0.10 to −0.04V),
platinum (+0.25 to +0.18V)

When first and second metallic materials are brought into contact in an aqueous environment, a galvanic couple is typically formed in which the first metallic material (i.e., the one with the more negative corrosion potential in the galvanic series) becomes the anode and corrodes more quickly than it would if it were not in contact with the second metallic material, while the second metallic material (i.e., the one with the more positive corrosion potential in the galvanic series) becomes the cathode and corrodes more slowly than it would if it were not in contact with the first metallic material. Either or both of the metallic materials in the pair may or may not corrode when disposed alone in the aqueous environment. Nonetheless, when two dissimilar metallic materials contact one another in the aqueous environment, the corrosion rates of each metallic material change, with the corrosion of the anode accelerating and corrosion of the cathode decelerating or even stopping.

A major factor affecting the rate of corrosion of the anode is the voltage difference between the two metals within the galvanic series—corrosion rates increase with increasing voltage differences. Another major factor affecting the rate of corrosion of the anode is the exposed area of the cathodic metallic material ($A_c$) relative to the exposed area of the anodic metallic material ($A_a$). The anode corrosion rate increase as the ratio $A_c:A_a$ increases.

Some specific embodiments of the invention will now be described with reference to the drawings. Referring to FIG. 1, a schematic, cross-sectional view of an implantable or insertable medical device 100 (e.g., a stent strut) is shown, in accordance with an embodiment of the invention. The device 100 is positioned against the wall of a blood vessel 220, which carries blood 210. The device 100 comprises (a) a first metallic region 110 having a first corrosion potential (e.g., magnesium, a magnesium alloy, etc.) and (b) a second metallic region 112 in electrical contact with the first metallic region 110 that has a second corrosion potential that is greater than the first corrosion potential (e.g., iron, an iron alloy, etc.). As an alternative to second metallic region 112, a first conductive polymeric region that has a second corrosion potential that is greater than the first corrosion potential (e.g., polypyrrole, etc.) may be employed. The medical device further comprises an ion-conductive polymeric region 116, which comprises an ion-conducting polymer and an ionic drug (specifically an anionic drug), disposed adjacent the second metallic region 112. As discussed in more detail below, ion-conductive polymeric regions are polymeric regions that support ion dissociation and allow ion movement. In the present case, the ion-conductive polymeric region contains one or more ionic drugs. The sides of the first and second metallic regions 110, 112, including the interface of these regions, is covered by a non-ion-conducting material region 114, for example, a non-ion-conducting polymeric region (e.g., selected from suitable non-ion-conducting homopolymers and copolymers listed in paragraph [54] of U.S. Patent Application Pub. No. 2003/0236514) or a non-ion-conducting inorganic region (e.g., a metal oxide, metal nitride, etc., for instance, a biodegradable phosphate glass such as that described in M. Bitar et al., *Journal of Materials Science: Materials In Medicine* 16 (2005) 1131-1136 or another biodegradable material such as magnesium fluoride), among others.

In the device 100 of FIG. 1, the first metallic region 110 is the anode, where the corrosion reaction can be designated $M \leftrightarrow M^{x+} + x\ e^-$ (e.g., $Mg^0 \rightarrow Mg^{2+} + 2e^-$; −2.37 V vs. SHE). The second metallic region 112 is the cathode. Various cathodic reactions are possible at the cathode. Commonly proposed reactions include (where dissolved oxygen is present):

$O_2 + 4H^+ + 4e^- \leftrightarrow 2H_2O$, where pH<7 (+1.229 V vs. SHE) and $O_2 + 2H_2O + 4e^- \leftrightarrow 4OH^-$, where pH≧7 (+0.401 V vs. SHE).

Other reactions include (e.g., where oxygen is not present):

$2H^+ + 2e^- \leftrightarrow H_2$, where pH<7 (0.0 V vs. SHE) and $2H_2O + 2e^- \leftrightarrow H_2 + 2OH^-$, where pH≧7 (−0.820 V vs. SHE).

Other reactions include reduction of metal ions that may be present within the blood.

Regardless of the precise reaction or reactions occurring at the cathode, as a result of the simultaneous oxidation and reduction processes, electrons flow from the anode (metallic region 110) to the cathode (metallic region 112) during in vivo galvanic corrosion. In order to maintain a suitable balance of charges, anions flow from the cathode to the anode, while cations flow from the anode to the cathode. In the system show in FIG. 1, the blood 210, the vessel wall 220 and the ion-conductive polymeric region 116 permit flow of ions. Moreover, because the drug in the ion-conductive polymeric region 116 is anionic, and because anions flow from the cathode to the anode during galvanic corrosion, the anionic drug in the ion-conductive polymeric region 116 is urged away from the cathode (metallic region 112) toward the blood vessel wall 220, thereby promoting delivery of the drug. Drug delivery may be enhanced by employing a porous ion-conductive polymeric region 116.

In the event that a cationic drug is provided in the ion-conductive polymeric region 116 of FIG. 1 (not shown), the cationic drug will be urged toward the cathode, with the galvanic corrosion process acting to retard delivery of the cationic drug.

In the device illustrated in FIG. 1 a single ion-conductive polymeric region 116 (i.e., a single layer) is shown. In other embodiments multiple ion-conductive polymeric regions, for example, multiple stacked layers, may be employed. For example, a first ion-conductive polymeric layer disposed on the cathode may contain a first higher mobility anionic drug, whereas a second ion-conductive polymeric layer disposed on the first ion-conductive polymeric layer may contain a second lower mobility anionic drug. In this scheme, the higher mobility drug in the lower layer encounters more resistance to drug delivery that the lower mobility drug in the upper layer.

In another example, an additional ion-conductive polymeric region may be placed in contact with the metallic region 110. Delivery of a cationic drug within such a polymeric region would be enhanced, whereas delivery of an anionic drug within such a polymeric region would be retarded. In the case of stent, such a drug would be released on the blood contacting side of the device. Examples of drugs for such embodiments include anti thrombotic drugs and drugs that promote endothelial cell growth.

To the extent that one may wish to slow the galvanic corrosion rate for the device of FIG. 1, one may, for example, decrease the exposed area of the cathodic metallic material 112 relative to the exposed area of the anodic metallic material 110, and vice versa. As another example, the galvanic corrosion rate for the device of FIG. 1 may be slowed by decreasing the ion mobility within the layer 116. As yet another example, a moderately conductive layer (not shown) may be provided between the anodic metallic region 110 and the cathodic metallic region 112 to slow galvanic corrosion. For example, an oxide layer (not shown) may be provided between the anodic metallic material 110 and cathodic metallic material 112. For instance, an oxide layer may be created and the technology described in U.S. Pat. No. 6,599,580 to Muffoletto et al. may be used to adjust the conductivity/resistivity of the oxide layer.

In another example, a moderately conductive layer may be provided between the ion-conductive polymeric region and an adjacent metallic region. For instance, with reference to FIG. 4, an oxide layer may be provided over the cathodic metallic region 112 and over a portion of the anodic metallic region 110. For instance, all sides of the anodic and cathodic regions 110, 112 may be initially covered by (e.g., by physical vapor deposition) with a non-conductive oxide layer 130n, and a portion of this layer removed from the anodic metallic region 110, for instance, by abrasion or ablation. (Alternatively, the anodic metallic region 110 may be partially masked prior to depositing the oxide layer 130n.) Subsequently, the conductivity of the oxide film is increased (e.g., using a method like that described in U.S. Pat. No. 6,599,580) within a portion of the oxide layer 130c that lies over the cathodic metallic region 112. The remaining portions of the oxide layer 130n remain untreated and thus non-conductive. Finally, an ion-conductive polymeric region 116 is provided over the conductive portion of the oxide layer 130. Such a design may be advantageous relative to that of FIG. 1 in that by applying the oxide layer, the adhesion of the ion-conductive polymeric region 116 to the structure may be increased.

Figure 2:
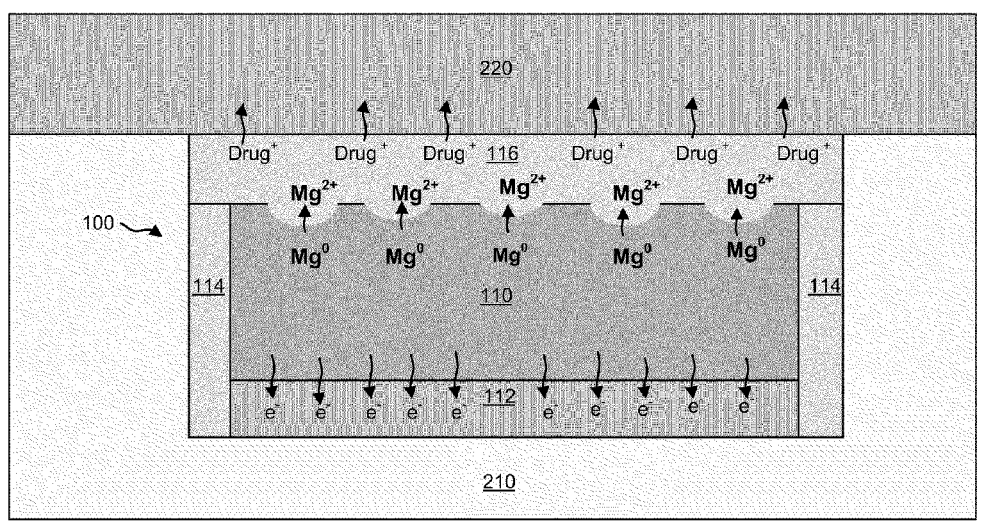
FIG. 2 is a schematic cross-sectional illustration of a medical device in accordance with another embodiment of the present invention, disposed in a blood vessel.

Referring now to FIG. 2, a schematic, cross-sectional view of an implantable or insertable medical device 100 (e.g., a stent strut) is shown, in accordance with another embodiment of the invention. The device 100 is positioned against a blood vessel 220, which carries blood 210. The device 100 comprises (a) a first metallic region 110 having a first corrosion potential (e.g., magnesium, a magnesium alloy, etc.) and (b) a second metallic region 112 in electrical contact with the first metallic region 110 having a second corrosion potential that is greater than the first corrosion potential (e.g., iron, an iron alloy, etc.). The medical device further comprises an ion-conductive polymeric region 116, which comprises an ion-conducting polymer and an ionic drug (e.g., a cationic drug), disposed adjacent the first metallic region 110. The sides of the first and second metallic regions 110, 112, including the interface of these regions, are covered by a non-ion-conducting material region 114.

In the device 100 of FIG. 2, the first metallic region 110 is the anode and the second metallic region 112 is the cathode. As a result of the simultaneous oxidation and reduction processes that occur during in vivo galvanic corrosion, electrons flow from the anode 110 to the cathode 112. In order to maintain a balance of charges, anions flow from the cathode to the anode, while cations flow from the anode to the cathode. As noted above, the drug in the ion-conductive polymeric region 116 of FIG. 2 is cationic. Thus, the cationic drug in the ion-conductive polymeric region 116 is urged away from the anode 110 and into the blood vessel wall 220, with the galvanic corrosion process acting to promote delivery of the drug.

Conversely, in the event that an anionic drug is provided in the ion-conductive polymeric region 116 of FIG. 2, the anionic drug will be urged toward the cathode, with the galvanic corrosion process acting to retard delivery of the anionic drug.

As with FIG. 1 above, moderately conductive layers may be included within the structure of FIG. 2 to slow drug release. Moreover, additional drug containing regions may be employed in the device of FIG. 2. For example, an ion-conductive polymeric region (not shown) may be placed in contact with the cathodic metallic region 112. Delivery of an anionic drug within such a polymeric region would be enhanced, whereas delivery of a cationic drug within such a polymeric region would be retarded.

Figure 3:
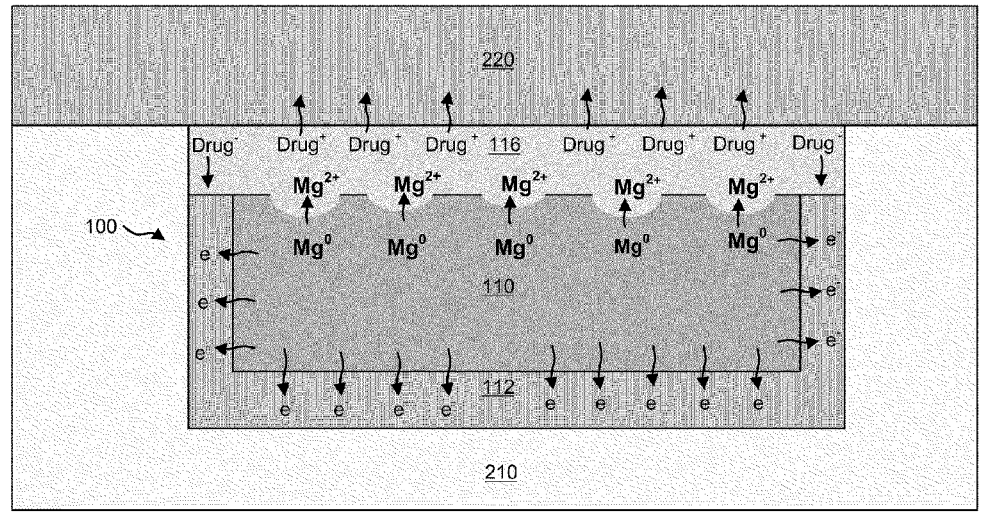
FIG. 3 is a schematic cross-sectional illustration of a medical device in accordance with yet another embodiment of the present invention, disposed in a blood vessel.
Figure 4:
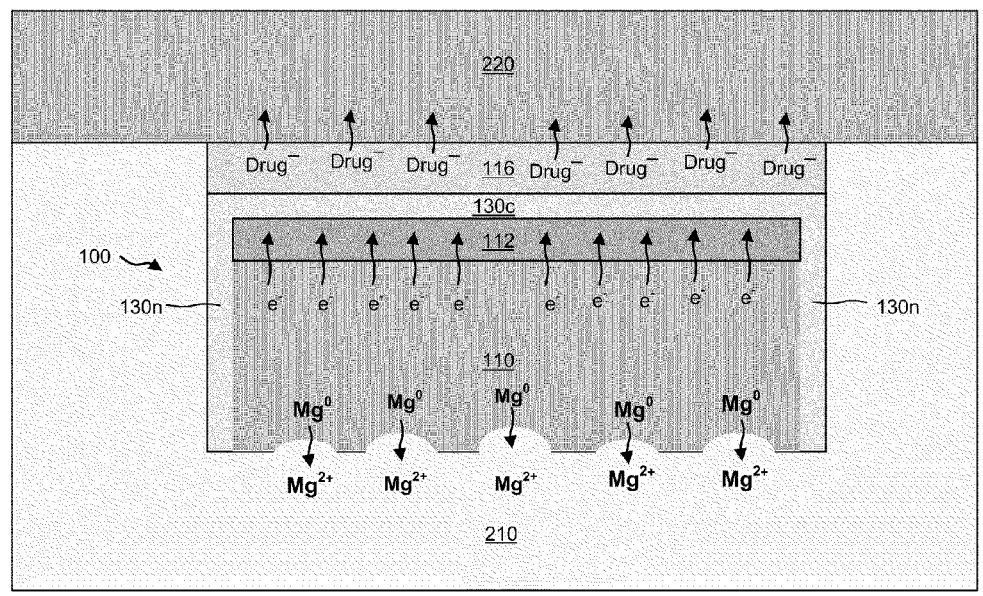
FIG. 4 is a schematic cross-sectional illustration of a medical device in accordance with still another embodiment of the present invention, disposed in a blood vessel.

Referring now to FIG. 3, a schematic, cross-sectional view of an implantable or insertable medical device 100 (e.g., a stent strut) is shown, in accordance with yet another embodiment of the invention. The device 100 is positioned against a blood vessel 220, which carries blood 210. The device 100 comprises (a) a first metallic region 110 having a first corrosion potential (e.g., magnesium, a magnesium alloy, etc.) and (b) a second metallic region 112 in electrical contact with the first metallic region 110 that has a second corrosion potential that is greater than the first corrosion potential (e.g., iron, an iron alloy, etc.). The medical device further comprises an ion-conductive polymeric region 116, which comprises an ion-conducting polymer and an ionic therapeutic agent (e.g., a cationic drug and an anionic drug), disposed adjacent the first metallic region 110 and the second metallic region 112. Unlike the devices of FIGS. 1, 2 and 4, the device of FIG. 3 does not comprise a non-ion-conducting material region 114 or a non-conducting oxide layer 130n, which covers the junction of the first and second metallic regions 110, 112.

In the device 100 of FIG. 3, the first metallic region 110 is the anode and the second metallic region 120 is the cathode. As a result of the simultaneous oxidation and reduction processes, electrons flow from the anode 110 to the cathode 112 during galvanic corrosion. In order to maintain a suitable balance of charges, anions flow from the cathode to the anode, while cations flow from the anode to the cathode. As noted above, the ion-conductive polymeric region 116 of FIG. 3 contains cationic and anionic drugs. Because cations flow away from the anode and toward the cathode, in some portions of the ion-conductive polymeric region 116 (i.e., those adjacent the anode 110) the cationic drug flows away from the underlying device, whereas in other portions of the ion-conductive polymeric region 116 (i.e., those adjacent the cathode 120) the cationic drug flows toward the underlying device. The converse is true of the anionic drug.

As previously indicated, in one aspect, the devices of the present invention contain the following elements: a first metallic region having a first corrosion potential, a second metallic region in electrical contact with said first metallic region and having a second corrosion potential that is greater than the first corrosion potential, and an ion-conductive polymeric region that comprises an ion conducting polymer and an ionic therapeutic agent.

Examples materials for use in forming the first and second metallic regions can be selected from suitable pairs of the following metals, among others: (a) substantially pure metals, including gold, platinum, palladium, iridium, osmium, rhodium, titanium, zirconium, tantalum, tungsten, niobium, ruthenium, alkaline earth metals (e.g., magnesium), iron and zinc, and (b) metal alloys, including metal alloys comprising iron and chromium (e.g., stainless steels, including platinum-enriched radiopaque stainless steel), niobium alloys, titanium alloys, nickel alloys including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys), and metal alloys such as those described in Pub. No. US 2002/0004060 A1, entitled "Metallic implant which is degradable in vivo," which include metal alloys whose main constituent is selected from alkali metals, alkaline earth metals, iron, and zinc, for example, metal alloys containing magnesium, iron or zinc as a main constituent and one or more additional constituents selected from the following: alkali metals such as Li, alkaline-earth metals such as Ca and Mg, transition metals such as Mn, Co, Ni, Cr, Cu, Cd, Zr, Ag, Au, Pd, Pt, Re, Fe and Zn, Group IIIa metals such as Al, and Group IVa elements such as C, Si, Sn and Pb (e.g., Mg alloys comprising Mg and one or more of Mg, Fe, Zn, Ca and Mn, Fe alloys comprising Fe and one or more of Mg, Zn, Ca and Mn and Zn alloys comprising Zn and one or more of Mg, Fe, Ca and Mn, among many others).

Some specific combinations of materials for the first and second metallic regions include following (wherein the first listed material is preferentially corroded galvanically relative to the second listed material): Mg/Zn, Mg alloy/Zn, Mg/Zn alloy, Mg alloy/Zn alloy, Zn/Al, Zn alloy/Al, Zn/Al alloy, Zn alloy/Al alloy, Mg/Fe, Mg alloy/Fe, Mg/Fe alloy, Mg alloy/Fe alloy, Zn/Fe, Zn/Fe alloy, Zn alloy/Fe, Zn alloy/Fe alloy, Mg/nitinol, Mg alloy/nitinol, Mg/inconel, Mg alloy/inconel, Mg/stainless steel, Mg alloy/stainless steel, Mg/platinum, Mg alloy/platinum, Zn/nitinol, Zn alloy/nitinol, Zn/inconel, Zn alloy/inconel, Zn/stainless steel, Zn alloy/stainless steel, Zn/platinum, Zn alloy/platinum, Fe/stainless steel, Fe alloy/stainless steel, Fe/nitinol, Fe alloy/nitinol, Fe/inconel, Fe alloy/inconel, Fe/platinum and Fe alloy/platinum, among many other possibilities. Those embodiments where iron is galvanically corroded may be useful in treating restenosis, as $Fe^{2+}$ has been reported to be a smooth muscle cell inhibitor.

Ion-conductive polymeric regions are polymeric regions that permit movement of ions, and in the present invention, permit movement of ionic therapeutic agents. Like other ionic species, ionic therapeutic agents move in response to concentration gradients (via a process called "diffusion") and in response to electric fields (via a process called "migration").

Ion-conductive polymeric regions are capable of providing therapeutic agents in an ionized form (via a process that is sometimes referred to as "solvation"), as opposed to a charge-neutral form (e.g., in the form of a non-ionized acid, non-ionized base, non-ionized salt, etc.), while at the same time allowing for ion movement. Charge-neutral species are generally not transported in response to an electric field (although they can undergo diffusion in response to a concentration gradient). Polymers suitable for maintaining therapeutic agents in ionized form commonly have cation and/or anion coordinating sites, which are capable of forming complexes with ions, or they are themselves ionized.

Suitable ion-conductive homopolymers and copolymers may be selected, for example, from the following: (a) polyethers, such as polyethylene oxide (PEO) (also referred to as polyethylene glycol, particularly at lower molecular weights) and polypropylene oxide (PPO), (b) polysiloxanes such as block copolymers of dimethyl siloxane and ethylene oxide, urethane crosslinked networks of poly(dimethyl siloxane-graft-ethylene oxide), and copolymers based on poly(methyl hydrosiloxane), poly(ethylene glycol)monomethyl ether and poly(ethylene glycol), see, e.g., Liang W-J. et al., "Morphology and Ionic Conductivity Studies of Hybrid Electrolytes based on Epoxide-Crosslinked Polysilane/Polyether Networks," *Macromol. Chem. Phys.* 2004, 205, 600-610, (c) polyphosphazenes such as methoxy ethoxy ethoxy polyphosphazene (MEEP), (d) poly(vinyl pyrrolidines), (e) polyacrylates and polymethacrylates such as poly(methoxy ethoxy ethyl methacrylate) (polyMEEMA) and poly[(ω-carboxy) oligooxyethylene methacrylate], (f) poly(crown ethers), and (g) other polymers, for instance itaconates such as poly[diethoxy(3)methyl itaconate] and poly(di-poly(propylene glycol)itaconate), succinates such as poly(ethylene succinate), adipates such as poly(ethylene adipate), poly(vinyl alcohols), poly(ethylene imines), poly(alkylene sulphides), poly(propiolactones), cellulose acetates, poly(vinyl methyl ketones), poly(hexamethylenevinylenes), poly(styrenes), poly(2-ethyl-2-oxazoline) and blends thereof, among many others.

In some embodiments, in order to enhance drug mobility, ion-conductive polymeric regions may contain one or more amorphous, low glass transition temperature ($T_g$) polymer chains. Without wishing to be bound by theory, it has been hypothesized that ion mobility increases with increasing polymer chain mobility, which in turn increases with decreasing Tg and decreasing crystallinity. Whether or not a polymeric material is amorphous can be determined by observing the thermal transitioning of the polymer matrix using a differential scanning calorimeter (DSC). As used herein, a "low $T_g$ polymer chain" is one displaying a $T_g$ that is below ambient temperature, more typically below about 20° C., below about 0° C., below about −25° C., or even below about −50° C. $T_g$ can be measured by any of a number of techniques including DSC. "Ambient temperature" is typically 25° C.-45° C., more typically body temperature (e.g., 35° C.-40° C.).

Optimal polymers for supporting ionization and transport of charged therapeutic agents within the ion-conducting polymeric regions of the present invention will vary from therapeutic agent to therapeutic agent, with suitable polymers for a given therapeutic agent being readily determined by those of ordinary skill in the art.

For instance, certain embodiments of the invention employ polymers that form ionized metal-salt complexes. PEO and its copolymers, for example, form complexes with a range of metal cations including alkali metal cations, alkaline earth metal cations, and transition metal cations. These include a number of mono and divalent cations, such as $Li^+$, $Na^+$, $K^+$, $Cs^+$, $Ag^+$, $Mg^{2+}$, $Ca^{2+}$, $Zn^{2+}$, $Cu^{2+}$ and so forth. Consequently, PEO is capable of stabilizing and transporting such cations, as well as counterions of the same, including various therapeutic agent counterions. In addition, PEO is capable of facilitating transport of uncharged therapeutic agents which are capable of complexing with metal cations. For example, it is known that silver ions simultaneously coordinate with olefins and with polymers, allowing the facilitated transport of olefins in a variety of polymers including, for example, PEO as well as cellulose acetate, poly(vinyl methyl ketone), poly(hexamethylenevinylene), poly(styrene), poly(N-vinyl pyrrolidone), and poly(2-ethyl-2-oxazoline), among others.

Certain other embodiments of the invention employ polyelectrolytes as ion-conductive polymers. Polyelectrolytes are polymers having multiple (e.g., 5, 10, 25, 50, 100, or more) charged sites (e.g., ionically dissociable groups), at least at the pH of the ion-conductive polymeric region. Depending on the type of dissociable groups, many polyelectrolytes may be classified as polyacids and polybases (and their salts). When dissociated, polyacids form polyanions, with protons being split off. Polybases, on the other hand, contain groups which are capable of accepting protons, thereby forming polycations. As defined herein, the term polyelectrolyte embraces a wide range of species, including polycations and their precursors (e.g., polybases and their salts), polyanions and their precursors (e.g., polyacids and their salts), polymers having both anionic and cationic groups (e.g., polymers having multiple acidic groups or their salts and multiple basic groups or their salts), ionomers (polyelectrolytes in which a small but significant proportion of the constitutional units carry charges), and so forth. Polyelectrolyte molecules may be crosslinked to increase stability. In some embodiments, biodegradable crosslinks may be employed to promote initial stability and ultimate biodegradability.

For example, ion-conductive polymeric regions in accordance with the present invention may contain an essentially immobile polyelectrolyte polycation or polyanion, as well as a mobile therapeutic agent of opposite charge. Analogous ion-conducting polymers in the rechargeable battery art are sometimes referred to as "single-ion polymer electrolytes".

In certain embodiments of the invention an acidic polymer may be reacted with a basic therapeutic agent to form a polyanion with a cationic drug as a counterion. In certain embodiments of the invention a basic polymer may be reacted with an acidic therapeutic agent to form a cation with an anionic drug as a counterion.

In addition to the polyelectrolytes listed above (e.g., itaconate, succinate, adipate, etc.), further specific examples from which suitable polyanions may be selected include poly(styrenesulfonate) polyanions, polyacrylic acid polyanions, alginate polyanions, eudragit polyanions, gelatin polyanions, hyaluronic acid polyanions, carrageenan polyanions, chondroitin sulfate polyanions, and carboxymethylcellulose polyanions, among many others. Specific examples from which suitable polycations may be selected include protamine sulfate polycations, poly(allylamine) polycations, polydiallyldimethylammonium polycations, polyethyleneimine polycations, chitosan polycations, gelatin polycations, spermidine polycations and albumin polycations, among many others.

As seen from the above, in some embodiments, biodegradable polymers are selected for use as ion-conductive polymers. A specific example of a biodegradable polymer which has been be used as an ion-conductive polymer is poly-epsilon-caprolactone. This polymer has demonstrated conductivities of $\sim 1 \times 10^{-6}$ S·cm$^{-1}$ with lithium salts, and conductivities of $\sim 2 \times 10^{-4}$ S·cm$^{-1}$ where plasticized. Biodegradation was found to be increased for the salt, which was attributed to an increase in the amorphous phase with salt addition, increasing the rate of biodegradation. For further information, see, e.g., C. P. Fonseca et al., "Development of a biodegradable polymer electrolyte for rechargeable batteries," *Journal of Power Sources* 155 (2006) 381-384 and C. P. Fonseca et al., "Thermal and Conduction Properties of a PCL-biodegradable Gel Polymer Electrolyte with LiClO4, LiF3CSO3, and LiBF4 Salts," *Int. J. Electrochem. Sci.,* 2 (2007) 52-63. Other examples of a biodegradable ion-conductive polymers include polylactic acid, for instance, poly(l-lactide) and poly(d,l-lactide). See, e.g., K, Shinyama et al., *Proceedings of the 7th International Conference on Properties and Applications of Dielectric Materials*, Jun. 1-5 2003 Nagoya, Japan, 707-710 and V. Maquet et al., *Langmuir* 2000, 16, 10463-10470.

In some embodiments, block copolymers may be utilized, which contain (a) one or more ion-conductive chains such as those described above and (b) one or more additional polymer chains which may be ion-conductive or non-ion-conductive chains (selected, for example, from chains based on the various homopolymers and copolymers listed in paragraph [54] of U.S. Patent Application Pub. No. 2003/0236514). Specific examples of additional polymer chains include biodegradable polycarbonate, polyanhydride and polyester chains, for example, polyester homopolymers and copolymers such as polyglycolide, poly-L-lactide, poly-D-lactide, poly-D,L-lactide, poly(beta-hydroxybutyrate), poly-D-gluconate, poly-L- gluconate, poly-D,L-gluconate, poly(epsilon-caprolactone), poly(delta-valerolactone), poly(p-dioxanone), poly(trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], poly(sebacic acid-co-fumaric acid), and poly(ortho esters) such as those synthesized by copolymerization of various diketene acetals and diols, among others. Specific examples of polymers include poly(l-lactide), poly(d,l-lactide), poly(d,l-lactide-co-glycolide), polycaprolactone, poly(ethylene oxide)-block-poly(l-lactide), poly(ethylene oxide)-block-poly(d,l-lactide), poly(ethylene oxide)-block-poly(d,l-lactide-co-glycolide) and poly(ethylene oxide)-block-polycaprolactone.

In some embodiments of the invention, radiopaque ion-conducting polymers may be employed, including iodo-substituted ion-conducting polymers. As a specific example, B. Nottelet et al., *Biomaterials*, 27 (2007) 4948-4954 describe the synthesis of poly(epsilon-caprolactone-co-alpha-iodo-epsilon-caprolactone) by binding iodine to polycaprolactone chains bearing carbanionic sites using lithium diisopropylamide according to the following scheme:

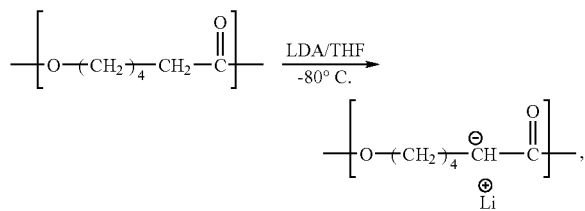

which is then followed by

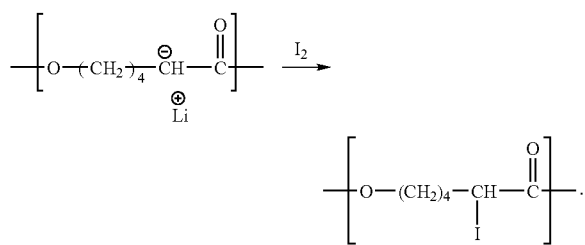

Ion-conductive polymeric regions for use in various embodiments of the invention may also be provided with components in addition to an ion-conducting polymers and ionic therapeutic agents.

For example, in some embodiments, an ion-conductive polymeric region may be provided with one or more plasticizers. In this regard, ion mobility within ion-conductive polymeric regions is also known to be enhanced by the use of plasticizers. Examples plasticizers for the ion-conductive polymeric regions of the present invention include the following among others: (a) unsaturated oils, such as peanut oil, sunflower oil, safflower oil and rapeseed oil, and expoxidized unsaturated oils, such as epoxidized soybean oil and epoxidized rapeseed oil, among others, (b) polyols including ethylene glycol, propylene glycol, glycerol, sorbitol, polyethylene glycol and polypropylene glycol, among others, (c) alkyl esters of polyols, for example, C1-C6 alkyl esters of polyols (such as glycerol) and short chain polethylene glycols, for instance, glyceryl triacetate (triacetin) and triethyleneglycol diacetate, among others, (d) alkyl esters of polycarboxylic acids, including diacids (e.g., C1-C4 dialkyl phthalates including dimethyl phthalate, diethyl phthalate, C1-C4 dialkyl esters of C4-C8 alpha-omega diacids such as diethyl succinate, etc.), triacids (e.g., citric acid C1-C4 alkyl triesters such as triethyl citrate, etc.)

As another example, in some embodiments, chelating agents may also be provided within the ion-conductive polymeric regions of the invention, in order to form chelates with the metal ions that are being released from the metallic region acting as the anode within the galvanic couple. For example, chelating agents such as chlorophyll may be used to form chelates with magnesium ions. This may be advantageous, for example, in that the formation of metal oxide/hydroxide particles at the anode may be prevented.

As another example, in some embodiments, inorganic materials may also be provided within the ion-conductive polymeric regions of the invention. For instance, such regions may contain (a) one or more polymeric phases that contain ion-conducting polymers and (b) one or more inorganic phases that contain inorganic materials. In some cases, the polymeric and inorganic phases may interact with one another by relatively weak forces (e.g., Van der Waals forces, ionic forces, hydrogen bonding, and so forth). In other cases, these phases are linked together through stronger forces (e.g., covalent bonds, coordination bonding, and ionic-coordination bonding). Examples of inorganic materials include metal (e.g., Ti, Zr, Nb, Ta, Ir, etc.) and semi-metal (e.g., C, Si, Ge, etc.) oxides, hydroxides, nitrides, carbide, oxonitrides and oxocarbides Specific examples include semimetal oxides (e.g., silicon oxide, for example, fumed silica, etc.) and metal oxides (e.g., titanium oxide, iridium oxide, zirconium oxide, tantalum oxide and niobium oxide, etc.), and polyoxometalates, among many others See, e.g., Gomez-Romero, P. et al., "Hybrid Organic-Inorganic Materials—In Search of Synergic Activity," *Adv. Mater.* 2001, 13, No. 3, Feb. 5, 163-174; Zhonghua Peng, "Rational Synthesis of Covalently Bonded Organic-Inorganic Hybrids," *Angew. Chem. Ind. Ed.*, 2004, 43, 930-935; Beleze, F. A. et al., "Synthesis and Characterization of Organic-Inorganic Hybrids Formed between Conducting Polymers and Crystalline Antimonic Acid," *J. Braz. Chem.*, Vol. 12, No. 4, 542-547, 2001; MacLachlan M. J. et al., "New (Inter)Faces: Polymers and Inorganic Materials," *Adv. Mater.*, 2000, 12, No. 9, pp. 675 et seq.

As noted above, ion-conductive polymeric regions in accordance with the invention contain at least one ionic therapeutic agent. As used herein, an ionic therapeutic agent is one have one or more positively charged groups, one or more negatively charged groups, or a combination of positively and negatively charged groups (although therapeutic agents with positive and negative charges will need a net charge to undergo migration).

Some therapeutic agents are inherently ionic. A few examples of inherently cationic therapeutic agents include amiloride, digoxin, morphine, procainamide, and quinine, among many others. Examples of anionic therapeutic agents include heparin and DNA, among many others.

In some embodiments, ionic therapeutic agents are formed by including in the ion-conductive polymeric region a charged species which coordinates/complexes with an uncharged therapeutic agent.

Other therapeutic agents can be modified to create ionic therapeutic agents. For example, a therapeutic agent may be rendered ionic by chemically modified the therapeutic agent to provide it with one or more charged functional groups.

For instance, conjugation of water insoluble or poorly soluble drugs, including anti-tumor agents such as paclitaxel, to hydrophilic polymers has recently been carried out in order to solubilize the drugs (and in some cases to improve tumor targeting and reduce drug toxicity). Similarly, cationic or anionic versions of water insoluble or poorly soluble drugs have also been developed. Taking paclitaxel as a specific example, cationic forms of this drug are known, including paclitaxel N-methyl pyridinium mesylate, as are various anionic forms of paclitaxel, including conjugates of paclitaxel with anionic polypeptides such as polyglutamic acid, polyaspartic acid, poly(glutamic acid-co-asparitc acid), specific examples of which include paclitaxel-poly(l-glutamic acid), paclitaxel-poly(l-glutamic acid)-PEO. See, e.g., U.S. Pat. No. 6,730,699; Duncan et al., *Journal of Controlled Release,* 74 (2001)135; Duncan, *Nature Reviews/Drug Discovery,* Vol. 2, May 2003, 347; J. G. Qasem et al, AAPS PharmSciTech 2003, 4(2) Article 21. In addition to these, U.S. Pat. No. 6,730,699, also describes paclitaxel conjugated to various other charged polymers including poly(d-glutamic acid), poly(dl-glutamic acid), poly(l-aspartic acid), poly(d-aspartic acid), poly(dl-aspartic acid), poly(l-lysine), poly(d-lysine), poly(dl-lysine), copolymers of the above listed polyamino acids with polyethylene glycol (e.g., paclitaxel-poly(l-glutamic acid)-PEO), as well as poly(2-hydroxyethyl 1-glutamine), chitosan, carboxymethyl dextran, hyaluronic acid, human serum albumin and alginic acid. Such materials may, of course, be conjugated with therapeutic agents other than paclitaxel, including olimus-family drugs such as sirolimus and everolimus, among other therapeutic agents, including those listed below. Still other forms of paclitaxel include carboxylated forms such as 1'-malyl paclitaxel sodium salt (see, e.g. E. W. DAmen et al., "Paclitaxel esters of malic acid as prodrugs with improved water solubility," *Bioorg. Med. Chem., Februrary* 2000, 8(2), pp. 427-32). Polyglutamate paclitaxel, in which paclitaxel is linked through the hydroxyl at the 2' position to the Δ carboxylic acid of the poly-L-glutamic acid (PGA), is produced by Cell Therapeutics, Inc., Seattle, Wash., USA. (The 7 position hydroxyl is also available for esterification.) This molecule is said to be cleaved in vivo by cathepsin B to liberate diglutamyl paclitaxel. In this molecule, the paclitaxel is bound to some of the carboxyl groups along the backbone of the polymer, leading to multiple paclitaxel units per molecule. For further information, see, e.g., R. Duncan et al., "Polymer-drug conjugates, PDEPT and PELT: basic principles for design and transfer from the laboratory to clinic," *Journal of Controlled Release* 74 (2001) 135-146, C. Li, "Poly(L-glutamic acid)-anticancer drug conjugates," *Advanced Drug Delivery Reviews* 54 (2002) 695-713; Duncan, *Nature Reviews/Drug Discovery*, Vol. 2, May 2003, 347; Qasem et al, AAPS PharmSciTech 2003, 4(2) Article 21; and U.S. Pat. No. 5,614,549.

A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth. Loadings may vary, for example, from 1 wt % or less, to 2 wt % to 5 wt % to 10 wt % to 20 wt % or more.

Examples of therapeutic agents for use in the medical devices of the present invention vary widely and may be selected from suitable members of the following, among others: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, and (ff) phospholipids including phosphorylcholine, phosphatidylinositol and phosphatidylcholine.

Some preferred therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TFG-β pathway agents such as polyanionic agents (heparin, fucoidin), decorin, and TFG-β antibodies, EGF pathway agents such as EGF antibodies, receptor antagonists and chimeric fusion proteins, TNF-α pathway agents such as thalidomide and analogs thereof, Thromboxane 2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic agents useful for the practice of the present invention are also disclosed in U.S. Pat. No. 5,733,925 to Kunz.

Ion-conductive polymeric regions for use in the present invention may be formed using a variety of techniques, for example, they may be formed from a solution that contains the following: (a) one or more ion-conducting polymers and (b) one or more solvent species such as water, tetrahydrofuran, acetonitrile, ethanol, methanol, among many others. If desired, various other agents may be added such as (c) one or more ionic therapeutic agents, (d) one or more plasticizers, (e) one or more crosslinking agents, (f) an inorganic component, and so forth. As another example, if the ion-conductive polymeric region contains at least one polymer with thermoplastic characteristics, then a melt may be formed, for example, that contains element (a) above and optionally elements (c), (d), (e) and/or (f), among other possibilities. Such a solution or melt may then be applied to a substrate (e.g., a medical device substrate having first and second metallic regions of differing corrosion potentials, a detachable substrate such as a mold, etc.) by a variety of techniques including pouring, dipping, spraying, extrusion, coating with an applicator (e.g., by roller or brush), spin-coating, web coating, ink jet techniques, and combinations of these processes, among others.

EXAMPLE 1

A 20 cm long magnesium rod (Goodfellow Metals, Cambridge, UK, MG007915-magnesium rod; diameter: 3.2 mm;

purity: 99.9%) is provided with 0.3 micrometer thick zinc coating via the following steps: 1. Activation in oxalic acid solution (oxalic acid 5.0 g/l; bath temperature 20-25 degrees C., treatment time 30 seconds) 2. Water rinse. 3. Activation in pyrophosphate bath (potassium pyrophosphate 10.0 g/l, pH 10.5; bath temperature 80 degrees C.; treatment time 30 seconds). 4. Water rinse. 5. Chemical zincating: zinc sulphate 50 g/l, potassium pyrophosphate 150 g/l, potassium fluoride 7 g/l, sodium carbonate 5 g/l, pH 10.2-10.5; bath temperature 60-65 degrees C.; treatment time 3 minutes. 6. Water rinse.

A small centered hole, diameter 2.8 mm, 18 mm deep is made by small-hole electrical discharge machining (EDM). Then, an ultrashort laser (Spectra-Physics Lasers, SPITFIRE, a commercial femtosecond Ti:sapphire laser and amplifier system) is used to cut a stent pattern through the wall of the EDM machined end section, as well as separating the tube section from the rod, using a laser with a pulse duration of 220 femtosecond and a fluence of 0.6 J/cm$^2$ at a wavelength of 780 nm with a repetition rate of 1 kHz. In order to provide the wall of the stent with a non-conductive layer, a PTFE film is deposited on the metal structure by pulsed laser deposition (PLD) technique using a KrF 248 nm excimer laser (Lambda Physik GmbH, COMPex 205) at a repetition rate of 10 Hz. The laser energy density used throughout the experiment is fixed at 1 J/cm$^2$. Deposition is performed in a vacuum chamber that is evacuated to a pressure of 20 mTorr. The inner (luminal) surface of the stent is protected from deposition by inserting a close fitting stainless steel pin into the interior. The PTFE layer as deposited on the outer (abluminal) surface is removed after the PLD step using the same excimer laser setting and focusing the laser beam tangent to the outer surface, leaving only the sides of the stent struts (including the magnesium/zinc junction covered with PTFE.

Finally a ion-conductive polymeric layer is deposited on the zinc surface by roller-coating the stent while mounted on a pin over a metal flat surface that is provided with a layer of the following solution: PEO Sigma Aldrich, MW 400 k, 10% (w/v), paclitaxel-poly(l-glutamic acid) formed as described in U.S. Pat. No. 6,884,817 to Li et al., 2% (w/v), balance DI water. Upon drying, the stent has an abluminal layer that contains 16.7 wt % paclitaxel-poly(d-glutamic acid) and 83.3% PEO.

EXAMPLE 2

The procedure of Example 1 is repeated with everolimus-poly(d-glutamic acid) as the therapeutic agent.

EXAMPLE 3

The procedure of Example 1 is repeated with poly-epsilon-caprolactone as the ion conductive polymer in a suitable solvent such as ethyl acetate, methylene chloride, chloroform, acetone, dimethyl formamide or tetrahydrofuran.

EXAMPLE 4

The procedure of Example 1 is repeated with poly(l-lactide), poly(d,l-lactide), poly(d,l-lactide-co-glycolide), poly (l-lactide)-block-PEO, poly(d,l-lactide)-block-PEO or poly (d,l-lactide-co-glycolide)-block-PEO as an ion conductive polymer in a suitable solvent such as ethyl acetate, methylene chloride, chloroform, acetone, dimethyl formamide or tetrahydrofuran.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising: (a) a first metallic region having a first corrosion potential, (b) a second metallic region in electrical contact with the first metallic region and having a second corrosion potential that is greater than the first corrosion potential, such that a galvanic couple is formed upon immersion of the medical device in normal saline with the first metallic region acting as an anode and the second metallic region acting as a cathode and (c) a solid ion-conductive polymeric region comprising an ion-conducting polymer and an ionic therapeutic agent, wherein the solid ion-conductive polymeric region is disposed on the first metallic region, the second metallic region, or both.

2. The medical device of claim 1, wherein the medical device is a stent.

3. The medical device of claim 1, wherein the first and second metallic regions are bioresorbable.

4. The medical device of claim 1, wherein the first metallic region is bioresorbable and the second metallic region is biostable.

5. The medical device of claim 1, wherein the first and second metallic regions are formed from materials selected from the following pairs of materials: Mg/Zn, Mg alloy/Zn, Mg/Zn alloy, Mg alloy/Zn alloy, Zn/Al, Zn alloy/Al, Zn/ Al alloy, Zn alloy/Al alloy, Mg/Fe, Mg alloy/Fe, Mg/Fe alloy, Mg alloy/Fe alloy, Zn/Fe, Zn/Fe alloy, Zn alloy/Fe, Zn alloy/ Fe alloy, Mg/nitinol, Mg alloy/nitinol, Mg/stainless steel, Mg alloy/stainless steel, Zn/nitinol, Zn alloy/nitinol, Zn/stainless steel, Zn alloy/stainless steel, Fe/stainless steel, Fe alloy/ stainless steel, Fe/nitinol, Fe alloy/nitinol.

6. The medical device of claim 1, wherein the ion-conductive polymer is a biostable polymer.

7. The medical device of claim 1, wherein the ion-conductive polymer is a biodegradable polymer.

8. The medical device of claim 1, wherein the ion-conductive polymer is a biodegradable polyester.

9. The medical device of claim 1, wherein the ion-conductive polymer is selected from epsilon-polycaprolactone, poly (d,l-lactide), poly(d,l-lactide-co-glycolide), a block copolymer comprising a poly(ethylene oxide) block and a polymer block selected from one or more of polycaprolactone, poly (d,l-lactide) and poly(d,l-lactide-co-glycolide).

10. The medical device of claim 1, wherein the ionic therapeutic agent is selected from an ionic antirestenotic agent, an ionic antithrombotic agent and an ionic agent for promoting epithelial cell growth.

11. The medical device of claim 1, wherein an interface between the first and second metallic regions is covered by a non-ion-conductive material.

12. The medical device of claim 1, wherein the solid ion-conductive polymeric region is porous.

13. The medical device of claim 1, wherein the solid ion-conductive polymeric region is disposed on the first metallic region.

14. The medical device of claim 13, wherein the ionic therapeutic agent is a cationic therapeutic agent.

15. The medical device of claim 13, wherein the ionic therapeutic agent is an anionic therapeutic agent.

16. The medical device of claim 1, wherein the solid ion-conductive polymeric region is disposed on the second metallic region.

17. The medical device of claim 16, wherein the ionic therapeutic agent is a cationic therapeutic agent.

18. The medical device of claim 16, wherein the ionic therapeutic agent is an anionic therapeutic agent.

19. The medical device of claim 1, wherein the solid ion-conductive polymeric region is disposed on both the first and second metallic regions.

20. The medical device of claim 19, wherein the solid ion-conductive polymeric region comprises a cationic therapeutic agent and an anionic therapeutic agent.

21. The medical device of claim 1, wherein the solid ion-conductive polymeric region is radio-opaque.

22. The medical device of claim 1, wherein the solid ion-conductive polymeric region further comprises a chelating agent.

23. The medical device of claim 1, wherein the solid ion-conductive polymeric region further comprises a plasticizer.

24. The medical device of claim 1, wherein the solid ion-conductive polymeric region further comprises inorganic particles.

25. The medical device of claim 1, wherein the solid ion-conductive polymeric region comprises (a) a first solid ion-conductive polymeric layer, comprising a first ion-conducting polymer and a first ionic therapeutic agent, disposed on the first metallic region and (b) a second solid ion-conductive polymeric region layer, comprising a second ion-conducting polymer and a second ionic therapeutic agent, disposed on the first solid ion-conductive polymeric layer, wherein the first and second ion-conducting polymers may be the same or different and wherein the first ionic therapeutic agent has a higher mobility than the second ionic therapeutic agent.

* * * * *